US010081748B2

(12) United States Patent
John et al.

(10) Patent No.: US 10,081,748 B2
(45) Date of Patent: Sep. 25, 2018

(54) METHODS FOR THICKENING HYDROPHOBIC LIQUIDS WITH AMPHIPHILIC ESTERS

(75) Inventors: George John, Edison, NJ (US); Swapnil R. Jadhav, Decatur, IL (US); Praveen Kumar Vemula, Cambridge, MA (US)

(73) Assignee: The Research Foundation of The City University of New York, New York, NY (US)

(*) Notice: Subject to any disclaimer, the term of this patent is extended or adjusted under 35 U.S.C. 154(b) by 324 days.

(21) Appl. No.: 13/387,536

(22) PCT Filed: Jul. 29, 2010

(86) PCT No.: PCT/US2010/043705
§ 371 (c)(1),
(2), (4) Date: Apr. 23, 2012

(87) PCT Pub. No.: WO2011/014653
PCT Pub. Date: Feb. 3, 2011

(65) Prior Publication Data
US 2012/0201863 A1    Aug. 9, 2012

Related U.S. Application Data

(60) Provisional application No. 61/229,553, filed on Jul. 29, 2009.

(51) Int. Cl.
| | | |
|---|---|---|
| C09K 8/58 | (2006.01) | |
| C09K 3/32 | (2006.01) | |
| C10G 33/04 | (2006.01) | |
| B01D 17/05 | (2006.01) | |
| A61K 9/00 | (2006.01) | |
| A61K 8/60 | (2006.01) | |
| A61Q 19/00 | (2006.01) | |
| A23D 9/013 | (2006.01) | |
| C09K 8/32 | (2006.01) | |
| C11C 3/08 | (2006.01) | |
| A23L 29/20 | (2016.01) | |
| A23L 33/10 | (2016.01) | |

(52) U.S. Cl.
CPC ............ C09K 3/32 (2013.01); A23D 9/013 (2013.01); A23L 29/20 (2016.08); A23L 33/10 (2016.08); A61K 8/60 (2013.01); A61Q 19/00 (2013.01); C09K 8/32 (2013.01); C11C 3/08 (2013.01); *A61K 2800/48* (2013.01)

(58) Field of Classification Search
CPC .. A23D 9/013; A23L 1/05; A23L 1/30; A61K 2800/48; A61K 8/60; A61Q 19/00; C09K 3/32; C09K 8/32; C11C 3/08
See application file for complete search history.

(56) References Cited

U.S. PATENT DOCUMENTS

| | | | |
|---|---|---|---|
| 3,649,647 A | 3/1972 | Ota et al. | |
| 3,861,466 A * | 1/1975 | Gale | 166/270.1 |
| 4,432,881 A * | 2/1984 | Evani | 507/121 |
| 5,981,464 A | 11/1999 | He et al. | |
| 6,200,784 B1 | 3/2001 | Jimenez et al. | |
| 6,632,952 B1 * | 10/2003 | Daniels | 554/178 |
| 6,939,420 B2 * | 9/2005 | Pollack | C06B 47/145 149/2 |
| 2004/0037795 A1 | 2/2004 | Hammer et al. | |
| 2005/0112161 A1 * | 5/2005 | Luo et al. | A61K 8/042 424/401 |

FOREIGN PATENT DOCUMENTS

| | | |
|---|---|---|
| CN | 20041027471 | 6/2004 |
| GB | 1532783 | 11/1978 |
| JP | 56024477 A * | 3/1981 |
| JP | 56024478 A * | 3/1981 |
| WO | WO9409639 | 5/1994 |
| WO | WO0124748 | 4/2001 |
| WO | WO2007007978 | 1/2007 |

OTHER PUBLICATIONS

Gomez et al., Grasas y aceites, 1986, 37(3), 137-140.*
Herrera et al., Grasas Y Aceites, 1986, 37(3), 137-140 (English Translation pp. 1-19).*
Murdan et al., Journal of Pharmaceutical Sciences, 88(6) pp. 608-614. (Year: 1999).*
Chopineau et al., Production of Biosurfactants from Sugar Alcohols and Vegetable Oils Catalyzed by Lipases in a Nonaqueous Medium, Biotechnology and Bioengineering, vol. 31, pp. 208-214 (1988).
Adebajo, M.O.; et al., "Porous Materials for Oil Spill Cleanup: A Review of Synthesis and Absorbing Properties," Porous Materials, vol. 10, pp. 159-170 (2003).
Bhattacharya, S., et al, "First Report of Phase Selective Gelation of Oil from Oil/Water Mixtures. Possible Implications Toward Containing Oil Spills," Chem. Commun., pp. 185-186 (2001).
Trivedi, D.R., et al., "Structure-Property Correlation of a New Family of Organogelators Based on Organic Salts and Their Selective Gelation of Oil from Oil/Water Mixtures," Chem, Eur. J., vol. 10, p. 5311-5322 (2004).
Daniel, J., et al., "Organogelation of Plant Oils and Hydrocarbons by Long-Chain Saturated FA, Fatty Alcohols, Wax Esters, and Dicarboxylic Acids," J. Am. Oil Chem. Soc., vol. 80, pp. 417-421 (2003).
Pernetti, M., et al., "Structuring of Edible Oils by Alternatives to Crystalline Fat," Curr. Opin. Colloid Interface Sci., vol. 12, pp. 221-231 (2007).
Wright, A.J., et al, "Formation, Structure, and Rheological Properties of Ricinelaidic Acid-Vegetable Oil Organogels," Am. Oil Chem. Soc. vol. 83, pp. 497-503 (2006).

(Continued)

*Primary Examiner* — Abigail Vanhorn
(74) *Attorney, Agent, or Firm* — Hoffmann & Baron, LLP (57) ABSTRACT

The present invention relates to a method for thickening a hydrophobic liquid. When a hydrophobic liquid is thickened in accordance with the invention, the liquid becomes significantly denser. Preferably, the hydrophobic liquid becomes a gel.

19 Claims, 5 Drawing Sheets

(56) References Cited

OTHER PUBLICATIONS

Gandolfo, F.G., et al., "Structuring of Edible Oils by Long-Chain FA, Fatty Alcohols, and their Mixtures," J.Am. Oil Chem. Soc., vol. 81, pp. 1-6 (2004).
Rogers, et al., "Oil Organogels: The Fat of the Future?." Soft Matter, vol. 5, pp. 1594-1596 (2009).
http://conference.abiosus.org/abstract/show/40. Short Chain Sugar Amphiphiles: Alternative Oil Structuring Agents (2009).
Vemula, et al., "Enzyme Catalysis: Tool to Make and Break Amygdalin Hydrogelators from Renewable Resources: A Delivery Model for Hydrophobic Drugs," J. Am. Chem. Soc., vol. 128, pp. 8932-8938 (2006).
Written Opinion of the International Searching Authority.
Jadhav, et al., "Sugar-Derived Phase-Selective Molecular Gelators as Model Solidifiers for Oil Spills", Angewandte, vol. 122, pp. 7861-7864; 2010.

\* cited by examiner

FIG. 1 (a) Open Chain Sugars (Sugar alcohols or polyhydric alcohols)
(b) Synthetic scheme of open chain sugar-based amphiphiles.

FIG. 2a Dynamic rheology of a 5 wt% M8 gel in diesel. Frequency Sweep

FIG. 2b Dynamic rheology of a 5 wt% M8 gel in diesel. Stress Sweep

FIG. 3a Micrograph of Self-assembled aggregates of open chain sugar amphiphiles in canola oil.
M8-optical FIG. 3b Micrograph of Self-assembled aggregates of open chain sugar amphiphiles in canola oil.
M8-SEM FIG. 3c Micrograph of Self-assembled aggregates of open chain sugar amphiphiles in canola oil.
S8-optical

12.6 μm

FIG. 3d Micrograph of Self-assembled aggregates of open chain sugar amphiphiles in canola oil.
S8-SEM

20 μm

FIG. 4 Optimized structures of M8 with possible stacking (linear bilayer).

FIG. 5

(Top) Schematic of phase selective gelation of oil from an oil-water mixture by the co-solvent method (avoiding the use of heat). (Bottom) Bulk phase selective gelation of diesel using the co-solvent method. (a) Diesel-water mixture (20:40 mL), (b) partial gelation of diesel observed after 1 hr. of injection of 8 mL of THF-mannitol saturated solution at the interface of the mixture, (c) diesel gel, strong enough to bear the weight of non-gelled water layer, obtained after allowing to set overnight, (d) 80% of diesel recovered from the diesel gel by vacuum distillation.

US 10,081,748 B2

METHODS FOR THICKENING HYDROPHOBIC LIQUIDS WITH AMPHIPHILIC ESTERS

CROSS-REFERENCE TO RELATED APPLICATION

The present application claims the benefit of U.S. Provisional Application No. 61/229,553, filed on Jul. 29, 2009.

BACKGROUND OF THE INVENTION

A need exists for improved methods for thickening, e.g., gelling, hydrophobic liquids. There are several reasons for the need for such methods.

Over the last twenty years, for example, the world has witnessed several marine oil spills releasing millions of gallons of oil into the ocean—the most notable being the 1989 Exxon Valdez incident that took place in Alaska, and more recently the explosion of a BP oil well, and resulting oil spill, in the Gulf of Mexico. Such haphazard oil spreads cause tremendous damage to the ecological system. The scale of such disasters has drawn attention to the need for new materials to contain oil spills and reclaim the oil. Many types of materials have been devised for oil spill control and cleanup, and several of these materials have been commercialized. However, problems exist with each of these current technologies.

Molecular gelators (MGs) are an alternate class of materials that may be used as solidifiers of oil. These are typically organic molecules of low molecular-weight that self-assemble into filaments or fibers in a variety of liquids. Despite the potential benefits, MGs are not currently used for oil spill treatment for various reasons. For example, many MGs are complex organic moieties that are potentially harmful to the environment. Furthermore, MGs are often specialized molecules that are synthesized by complex, multi-step procedures—in turn, it is doubtful whether the materials can be delivered at low cost and in large quantities that are required for a major oil spill. Also, the action of MGs requires their dissolution in the solvent, which is usually accomplished by heating a mixture of the MG powder and solvent up to a high temperature. This is impractical for oil spill treatment where it is imperative to be able to induce gelation of the oil under ambient conditions.

It is advantageous for the MG to be capable of phase-selective gelation (PSG), i.e., the MG should preferentially gel the oil layer even when it is in contact with the water. In other words, water should not impair the oil-gelling properties of the MG. This advantage can be challenging because many MGs are amphiphilic molecules, i.e., they have water-loving and water-hating parts, and this is a key to their gelling ability. When contacted with water, these molecules partition to the oil-water interface (thereby acting as surfactants or emulsifiers)—as a result, their gelling ability is affected. Due to the above challenges, only a few PSGs of the oil phase from an oil-water mixture have been reported. However, existing PSGs are complex molecules, they require heat to be dissolved in the solvent, and their environmental suitability is questionable—thus, the practical use of these PSGs for oil spill treatment is limited. There is a need for new and improved PSGs that can avoid the above problems.

Another application of methods for thickening hydrophobic liquids is in structuring vegetable oils. Currently, the most common methods use hypercholesterolemic fatty acids, such as stearic acid, as structuring agents. For edible oils, however, healthier methods are desirable.

There is also the need for gel-based formulations to enhance the delivery of drugs and increase the bioavailability of drugs at targeted regions of the body.

MGs may also be used in making oil in water microemulsions. The microemulsions may then be used to solubilize or encapsulate hydrophilic and hydrophobic molecules.

Another application of PSGs might be to covert fuel or crude oil fractions to solid-like material to facilitate the transportation of the fuels and prevent the spreading of liquids in the event of accidental or intentional fuel spills.

SUMMARY OF THE INVENTION

In one embodiment, the present invention relates to a method for thickening a hydrophobic liquid by contacting the hydrophobic liquid with an effective amount of an amphiphilic ester having the formula $ROC(O)R^1$. In each embodiment, RO— represents a moiety of a sugar alcohol, a monosaccharide or a disaccharide. Accordingly, the moiety RO— may have more than one oxygen atom, typically one or two, e.g., $RO[C(O)R^1]_m$.

In the formulas above, $R^1$ independently represents a branched or unbranched, saturated or unsaturated alkyl group having a minimum of 5 and a maximum of 11 carbon atoms, and m is 1 or 2. In another embodiment, $R^1$ independently represents a branched or unbranched, saturated or unsaturated alkyl group having a minimum of 2 and a maximum of 20 carbon atoms.

It is understood that the formula $ROC(O)R^1$ (or $RO[C(O)R^1]_m$) may be either a monoester (m=1) or a diester (m=2). Accordingly, a diester has the formula $RO[C(O)R^1]_2$.

In another embodiment, the invention relates to a method for separating a hydrophobic liquid phase from a mixture of the hydrophobic liquid phase and an aqueous phase. The method includes (a) contacting the hydrophobic liquid phase with an effective amount of an amphiphilic ester having the formula $ROC(O)R^1$ or $RO[C(O)R^1]_m$, and (b) separating the gelled hydrophobic liquid phase from the aqueous phase.

In another embodiment, the invention relates to a method for separating crude oil and water from a first mixture of a first crude oil phase and an aqueous phase. The method includes (a) contacting the first mixture with an effective amount of an amphiphilic ester having the formula $ROC(O)R^1$ or $RO[C(O)R^1]_m$, and (b) separating the gelled first crude oil phase from the aqueous phase.

In another embodiment, the invention relates to a method for structuring a liquid glyceride comprising contacting the glyceride with an effective amount of an amphiphilic ester having the formula $ROC(O)R^1$ or $RO[C(O)R^1]_m$.

In another embodiment, the invention relates to a method of encapsulating one or more pharmaceutically active ingredients. The method includes contacting one or more pharmaceutically active ingredients and a hydrophobic liquid with an effective amount of an amphiphilic ester having the formula $ROC(O)R^1$ or $RO[C(O)R^1]_m$.

In another embodiment, the invention relates to a method of making an oil in water emulsion. The emulsion is made by mixing an aqueous phase, an oil component, and an amphiphilic ester having the formula $ROC(O)R^1$ or $RO[C(O)R^1]_m$ until a microemulsion is formed. The oil component comprises a hydrophobic liquid.

In yet another embodiment, the invention relates to a method of transporting fuel or crude oil fractions. The method involves contacting the fuel or crude oil fractions with an effective amount of an amphiphilic ester having the formula ROC(O)R$^1$ or RO[C(O)R$^1$]$_m$ to form a gel, and transporting the gelled fuel or crude oil fractions.

DESCRIPTION OF FIGURES

FIG. 6 Bulk phase selective gelation of diesel using a new method. a, Diesel-water mixture (20:40 ml). b, Partial gelation of diesel observed after 1 hr. of injection of 8 ml of THF-mannitol 2 saturated solution at the interface of the mixture. c, Diesel gel, strong enough to bear the weight of non-gelled water layer, obtained after allowing to set overnight. d, 80% of diesel recovered from the diesel gel by vacuum distillation.

DETAILED DESCRIPTION

The present invention relates generally to a method for thickening a hydrophobic liquid. When a hydrophobic liquid is thickened in accordance with the invention, the liquid becomes significantly denser. Preferably, the hydrophobic liquid becomes a gel. The method comprises contacting the hydrophobic liquid with an amphiphilic ester having the formula ROC(O)R$^1$.

In another embodiment, the amphiphilic ester has the formula RO[C(O)R$^1$]$_m$, wherein m is one or two. When m is one, the formula represents a monoester. When m is two, the formula represents a diester. In other words, a diester has the formula R[OC(O)R$^1$]$_2$.

In one embodiment, RO— represents a moiety of a sugar alcohol, a monosaccharide or a disaccharide. Sugar alcohols are also known as hydrogenated saccharides, polyols, polyhydric alcohols, and polyalcohols. A moiety is a sugar alcohol, a monosaccharide or a disaccharide that has lost a hydrogen atom from a hydroxyl group, typically from a primary hydroxyl group.

Sugar alcohols have the general formula H(CHOH)$_n$H, and can be sugar alcohols of monosaccharides or disaccharides. When RO represents a moiety of a sugar alcohol of a monosaccharide, n is 4, 5, or, preferably, 6. Some examples of sugar alcohols wherein n is 4 include erythritol and threitol. Some examples of sugar alcohols wherein n is 5 include arabitol, xylitol, and ribitol. Some examples of sugar alcohols wherein n is 6 include mannitol, sorbitol, dulcitol and iditol. Some examples of sugar alcohols of disaccharides include maltitol and lactitol. In the preferred amphiphilic ester, RO— represents a moiety of mannitol or sorbitol.

Monosaccharides can be any combination of aldoses or ketoses; and of tetroses, pentoses, or hexoses. Some examples of monosaccharides include glucose, ribose, and fructose. Disaccharides are two monosaccharides joined by a glycosidic bond. Some examples of disaccharides include sucrose, lactose, maltose, and cellobiose.

In the formula for the amphiphilic ester, R$^1$ represents a branched or unbranched; or saturated or unsaturated alkyl group, in any of the four possible combinations. The minimum total number of carbon atoms in alkyl group R$^1$ is 5, and preferably 6. The maximum total number of carbon atoms in alkyl group R$^1$ is 11, preferably 10, more preferably 9, and most preferably 8. The optimum total number of carbon atoms in alkyl group R$^1$ is 7.

When m is two, R$^1$ independently represents a branched or unbranched, saturated or unsaturated alkyl group having a minimum of 5 and a maximum of 11 carbon atoms. Accordingly, an amphiphilic diester may contain two different alkyl groups.

Some examples of saturated alkyl groups include n-pentyl, n-hexyl, n-heptyl, n-octyl, n-nonyl, n-decyl, n-lauryl, iso-pentyl, iso-hexyl, iso-heptyl, iso-octyl, iso-nonyl, iso-decyl, iso-lauryl, 2,2-dimethylpropyl, 4-methyl-2-pentyl, 2,3-dimethylpentyl, 3-ethyl-2-pentyl, 2-isopropyl-2,2-dimethylpentyl, and 3-ethyl-5-methyloctyl. Other examples of saturated alkyl groups include n-undecanyl, n-dodecanyl, n-tridecanyl, n-tetradecanyl, n-pentadecanyl, n-hexadecanyl, n-heptadecanyl, n-octadecanyl, n-nonadecanyl, n-icosanyl, 4-methyldodecanyl, and 3-ethyl-5-methylpentadecanyl.

Some examples of unsaturated alkyl groups include n-pentenyl, n-hex-2-enyl, n-hept-3-enyl, n-oct-4-enyl, n-non-5-enyl, n-dec-6-enyl, n-dodec-3,6,-dienyl, iso-pentenyl, iso-hexenyl, iso-heptenyl, iso-octenyl, iso-nonenyl, iso-decenyl, iso-dodecenyl, 3,3,3-trimethylpropenyl, 4-methyl-2-pentenyl, 2,3-dimethylpent-2-enyl, 3-ethyl-2-pentenyl, 2-isopropyl-2,2-dimethylpentynyl, and 3-ethyl-5-methyloct-2,4-dienyl. Other examples of unsaturated alkyl groups include n-heptadec-3,6,-dienyl, 3-isopropyl-2,4-dimethylpentynyl, and 3,3,3-trimethylheptadecynyl.

A preferred alkyl group R$^1$ in the amphiphilic ester is n-heptyl (i.e., the group —C(O)R$^1$ is caprylyl). In a preferred amphiphilic ester, RO— is a moiety of mannitol or sorbitol, and —C(O)R$^1$ is caprylyl (i.e., R$^1$ is n-heptyl). A preferred amphiphilic ester is mannitoloctanoate.

In another embodiment, the minimum total number of carbon atoms in the alkyl group R$^1$ is 2, and preferably 6. The maximum total number of carbon atoms in alkyl group R$^1$ is 20, preferably 10, more preferably 9, and most preferably 8.

The hydrophobic liquid is any liquid that is insoluble in water. Some examples of hydrophobic liquids include a fatty acid, a mixture of fatty acids, a glyceride, a mixture of glycerides, or a mixture of fatty acids and glycerides. The fatty acids may be saturated or unsaturated, and typically have between 8 and 20 carbon atoms. Some fatty acids have between 2 and 20 carbon atoms. Liquid glycerides are typically mixtures of mono-, di-, and triglycerides of saturated and unsaturated fatty acids, usually predominantly triglycerides, and usually predominantly of unsaturated fatty acids. Such glycerides may, for example, be vegetable oils or fish oils.

Vegetable oils may be edible or non-edible, and may be extracted from any part of any plant that contains such oils. Some examples of vegetable oils include palm oil, soybean oil, rapeseed oil, sunflower seed oil, peanut oil, cottonseed oil, palm kernel oil, coconut oil, olive oil, and mixtures thereof.

Fish oils may be derived from any fish that contain such oils. Some examples of fish oils include the oils of sardines, herring, mackerel, trout, flounder, tuna, and salmon. Fish oils containing omega-3 fatty acids, such as, for example, (4Z,7Z,10Z,13Z,16Z,19Z)-docosa-4,7,10,13,16,19-hexaenoic acid (DHA) and (5Z,8Z,11Z,14Z,17Z)-eicosa-5,8,11, 14,17-pentaenoic acid (EPA), are especially preferred.

Other hydrophobic liquids that can be thickened in accordance with the invention include, for example, pheromones, and essential oils. Pheromones are chemical signals that trigger a natural response in another member of the same species. The species may be an insect, a plant or an animal. Any pheromone that is a hydrophobic liquid may be thickened in accordance with the invention. The pheromone may, for example, be an alarm pheromone, attack pheromone, sex pheromone, food trail pheromone, etc.

Essential oils are volatile aroma compounds from plants and trees, and may be obtained by any method from any part of any plant or tree that contains such oils. For example, essential oils may be obtained from flowers, leaves, wood, bark, roots, seeds, or peel. Some examples of methods by which essential oils may be obtained include steam distillation, pressing, and solvent extraction. Essential oils may be obtained by such methods, for example, from lavender, peppermint, eucalyptus, clove, rose, and citrus (e.g., lemon and orange) plants or trees.

In one embodiment, the invention relates to a method for separating a hydrophobic liquid phase from a mixture of the hydrophobic liquid phase and an aqueous phase. The method involves (a) contacting the hydrophobic liquid phase with an amphiphilic ester having the formula $ROC(O)R^1$, wherein the amphiphilic ester selectively gels the hydrophobic liquid phase, and (b) separating the gelled hydrophobic liquid phase from the aqueous phase. The amphiphilic ester, $ROC(O)R^1$, and its individual components, R and $R^1$, are as described above.

In another embodiment, the amphiphilic ester has the formula $RO[C(O)R^1]_m$, wherein m is one or two. The amphiphilic ester, $RO[C(O)R^1]_m$, and its individual components, R, $R^1$, and m, are as described above.

The hydrophobic liquid phase is made up primarily of a hydrophobic liquid, as described above. For example, the hydrophobic liquid phase may contain crude oil from a crude oil spill. The crude oil is any fraction of liquid petroleum, including low-boiling, intermediate, and high boiling fractions. The crude oil may, for example, contain one or more fractions selected from gasoline, kerosene, diesel fuel, heavy gas oil and lubricating oil.

The aqueous phase is a solution wherein the solvent is water. The aqueous phase may be acidic, neutral or alkaline, and may or may not include a salt, a detergent, or both. For example, the aqueous phase may be ocean water in the case of a crude oil spill.

The amphiphilic ester may be contacted with the hydrophobic liquid phase in any known manner. In a preferred embodiment, the amphiphilic ester is contacted with the hydrophobic liquid phase at the interface of the hydrophobic liquid phase and the aqueous phase. The amphiphilic ester may be contacted with the hydrophobic liquid phase at the interface of the hydrophobic liquid phase and the aqueous phase by methods that are well known in the art. For example, the amphiphilic ester may be injected at the interface using a syringe or pipette.

The amphiphilic ester is added to the hydrophobic liquid phase in an amount that causes the hydrophobic liquid phase to thicken sufficiently to be easily separated from the aqueous phase, and preferably to gel, i.e., an effective amount. The minimum amount of the amphiphilic ester is the minimum amount that causes the hydrophobic liquid phase to gel sufficiently to be easily separated from the aqueous phase. For example, the minimum amount of the amphiphilic ester may be as low as about 0.01% wt/vol, more typically about 0.05% wt/vol, and most typically about 0.5% wt/vol based upon the volume of the hydrophobic liquid phase. A convenient range is about 1 to about 2.5% wt/vol. It is usually not necessary to use more than about 5% wt/vol, although more can be used if necessary. For example, up to about 10% wt/vol may be used.

The amphiphilic ester may be added to the mixture in the absence of a solvent. Alternatively, the amphiphilic ester is dissolved in a solvent that is miscible with water before being added to the mixture. Preferred solvents possess a partition coefficient P having a value of at least about $300^{-1}$ wherein P represents solubility (v/v) in hydrophobic liquid phase/solubility (v/v) in aqueous phase. There is no necessary maximum value for P. For example, P may be $1,000^{-1}$ or even smaller.

Examples of suitable solvents include methyl alcohol, ethyl alcohol, propyl alcohol, iso-propyl alcohol, tert-butyl alcohol, dioxane, dimethylformamide (DMF), dimethyl sulfoxide (DMSO), acetone, tetrahydrofuran (THF) and acetonitrile. Another suitable solvent is methyl ethyl ketone.

The amphiphilic ester is preferably added to the first mixture at ambient temperature. In the case of an oil spill, for example, the amphiphilic ester is added to the first mixture at the temperature of the water into which the crude oil is spilled, e.g., lake, river, bay, sound, estuary, or ocean.

The amphiphilic ester selectively gels the crude oil in the first crude oil phase. The gelled first crude oil phase is easily and conveniently separated from the liquid aqueous phase.

In another embodiment of the invention, the method involves separating crude oil and water from a first mixture of a first crude oil phase and an aqueous phase. The method involves (a) contacting the first mixture with an amphiphilic ester having the formula $ROC(O)R^1$, and (b) separating the gelled first crude oil phase from the aqueous phase. The amphiphilic ester having the formula $ROC(O)R^1$ is as described above.

In another embodiment, the amphiphilic ester has the formula $RO[C(O)R^1]_m$, wherein m is one or two. The amphiphilic ester, $RO[C(O)R^1]_m$, and its individual components, R, $R^1$, and m, are as described above.

The amphiphilic ester is contacted with the first mixture also as described above, e.g., preferably, the amphiphilic ester is contacted with the hydrophobic liquid phase at ambient temperature and at the interface of the hydrophobic liquid phase and the aqueous phase, either without a solvent or with a solvent at a concentration of the amphiphilic ester in the solvent of 50% of saturation to 100% of saturation.

The amphiphilic ester selectively gels the crude oil in the first crude oil phase. The gelled first crude oil phase is now easily and conveniently separated from the aqueous phase by methods known in the art. For example, the gelled first crude oil phase may be separated from the aqueous phase by well known mechanical methods.

The method of the invention may further include separating the amphiphilic ester and the crude oil from the separated gelled first crude oil phase from part (b). The amphiphilic ester and the crude oil may, for example, be separated from the gelled first crude oil phase by distillation, preferably vacuum distillation. The crude oil may then be recovered from the distillate. The amphiphilic ester may separately be recovered from the residue.

The amphiphilic ester recovered by distillation may be reused for continuing to clean the same oil spill, or to clean a different oil spill. For example, additional steps (c) and (d) may be added to the method described above. Thus, the method may further include (c) contacting a second mixture of a second crude oil phase and an aqueous phase with the amphiphilic ester that was recovered from the gelled first crude oil phase by distillation and the recovered amphiphilic ester selectively gels the second crude oil phase and (d) separating the second gelled crude oil phase from the aqueous phase.

Alternatively, the crude oil may be separated from the gelled first crude oil phase by enzyme-mediated gel degradation. Suitable enzymes are those that cleave the linkages between alkylate moieties and the sugar alcohol/monosaccharide/disaccharide moieties of the amphiphilic ester. Suitable enzymes include hydrolases. The enzyme-mediated gel degradation may occur at ambient temperature.

In another embodiment, the invention relates to a method for structuring a liquid glyceride. The glyceride may be any of the glycerides mentioned above, especially vegetable oil. The method of this embodiment comprises contacting the glyceride with any of the amphiphilic esters described above. The amphiphilic ester may be added to the glyceride in any of the solvents described above, or without a solvent.

The structuring is carried at any suitable temperatures, as can be determined by those having skill in the art. As a general guideline, the reaction is carried out at a temperature of a minimum of about 10° C., preferably a minimum of about 20° C.; and a maximum of about 100° C., preferably a maximum of about 80° C., more preferably a maximum of about 70° C., most preferably a maximum of about 60° C. Ambient temperature is especially convenient.

The thickening (e.g., gelling, structuring, etc.) of a hydrophobic liquid in accordance with the invention takes place by adding a suitable amount of the amphiphilic ester (i.e., molecular gelator, MG) to the liquid. The specific amount of amphiphilic ester to be added to the hydrophobic liquid is any effective amount, and depends, inter alia, on the amount and structure of the hydrophobic liquid to be thickened and the amphiphilic ester used. See above.

In another embodiment, the invention relates to a method of encapsulating one or more pharmaceutically active ingredients. The method involves contacting one or more pharmaceutically active ingredients and a hydrophobic liquid with an effective amount of an amphiphilic ester having the formula $ROC(O)R^1$. The amphiphilic ester having the formula $ROC(O)R^1$, and its individual components, R and $R^1$, are as described above.

In another embodiment, the amphiphilic ester has the formula $RO[C(O)R^1]_m$, wherein m is one or two. The amphiphilic ester, $RO[C(O)R^1]_m$, and its individual components, R, $R^1$, and m, are as described above.

The hydrophobic liquid is also described above. In a preferred embodiment, the hydrophobic liquid is a vegetable oil.

The one or more pharmaceutically active ingredients include any suitable pharmaceutically active ingredient, e.g., hydrophilic and lipophilic drugs. The one or more pharmaceutically active ingredients may include one active ingredient, two active ingredients, three active ingredients, four active ingredients, etc.

Examples of hydrophilic drugs include, but are not limited to, polysaccharides and other macromolecular drugs such as peptides, proteins, peptidomimetics, cytokines, nucleotides, nucleosides, genetic materials, toxoids, and serum vaccines, nicotine, and caffeine. Polysaccharide drugs include a disaccharide, oligosaccharide, or longer chain saccharide polymer that is suitable for administration to a human being. Examples of polysaccharide drugs include glucosamine, glycosaminoglycans, dextran, xylan, pentasaccharide, polygalacturonic acid, polymannuronic acid, chitin, pharmaceutically acceptable salts, esters or other derivatives thereof, and combinations thereof. The polysaccharide drugs may also be fragments of naturally occurring or synthetic polysaccharides.

Examples of lipophilic drugs include, but are not limited to, bezafibrate, ibuprofen (both R- and S-isomers), nitrazepam, alprazolam, curcumin and other dyes.

The contacting of the one or more pharmaceutically active ingredients and the hydrophobic liquid with an effective amount of an amphiphilic ester may occur at any suitable temperature, as determined by those having skill in the art. The suitable temperature will not interfere with the activity of the one or more pharmaceutically active ingredients. As a general guideline, the reaction is carried out at a temperature of a minimum of about 10° C., preferably a minimum of about 20° C.; and a maximum of about 150° C. or 100° C., preferably a maximum of about 80° C., more preferably a maximum of about 70° C., most preferably a maximum of about 60° C. Ambient temperature is especially convenient.

In one aspect, the pharmaceutical actives are encapsulated by the hydrophobic liquid upon cooling, thereby, forming a gel matrix entrapping the actives. Encapsulation of the active ingredients enhances topical and transdermal delivery of the actives thereby increasing the bioavailability of the actives at targeted regions of the body.

In another aspect, the pharmaceutical actives are encapsulated by the hydrophobic liquid without cooling. For example, the encapsulation may occur at the reaction temperature, if the reaction temperature is ambient temperature.

An effective amount of amphiphilic ester is any amount sufficient to cause encapsulation or gelation of the hydrophobic liquid. An effective amount can be determined by a person having ordinary skill in the art. Examples of effective amounts of amphiphilic ester are discussed above.

In another embodiment, the invention relates to a method of making an oil in water emulsion. The methods involves mixing an aqueous phase, an oil component, with any of the amphiphilic esters described above, i.e., $ROC(O)R^1$ or $RO[C(O)R^1]_m$, until a microemulsion is formed.

The aqueous phase is a solution wherein the solvent is water. The aqueous phase may be acidic, neutral or alkaline, and may or may not include a salt, a detergent, or both.

The oil component comprises a hydrophobic liquid. Hydrophobic liquids are described above.

The aqueous phase and oil component may contain various other ingredients known to a person having ordinary skill in the art. For example, if the microemulsion is to be a cosmetic, then the aqueous and oil phases may contain excipients and actives suitable for use in a cosmetic. Likewise, if the microemulsion is to be a pharmaceutical, then the aqueous and oil phases may contain excipients and actives suitable for use in a pharmaceutical.

The mixing may occur by any means known to a person having ordinary skill in the art. For example, the mixing may occur using a homogenizer, sonicator, or vortex.

Suitable reaction conditions including temperature and percentages of ingredients are discussed above.

In another embodiment, the invention relates to a method of transporting fuel or crude oil fractions. The method involves contacting the fuel or crude oil fractions with an effective amount of any amphiphilic ester described above and transporting the gelled fuel or crude oil fractions.

Gelling fuel or crude oil is described above. The gelled fuel or crude oil may be transported by any means known in the art. For example, the gelled fuel or crude oil may be transported by truck, tanker, ship, car, train, airplane, etc.

The gelling of fuel or crude oil facilitates transportation of fuel or crude oil. In their liquid state, fuel or crude oil pose risks of spillage during transportation. Gelling of fuel or crude oil prevents the spreading of liquids in the event of accidental or intentional spillage.

Synthesis and Testing of Amphiphilic Esters, e.g., Molecular Gelators (MGs)

The amphiphilic esters may be made by methods known in the art. For example, the amphiphilic esters are conveniently made by an enzyme-mediated trans-esterification reaction of a sugar alcohol, a monosaccharide or a disaccharide and an ester, e.g., a vinyl ester, having an appropriate acyl group as described above, i.e., —C(O)R$^1$, under suitable reaction conditions. A suitable enzyme is Novozyme 435. Suitable reaction conditions include, for example, a suitable solvent, e.g., acetone, at 40-60 degrees centigrade. See FIG. 1.

Figure 1:
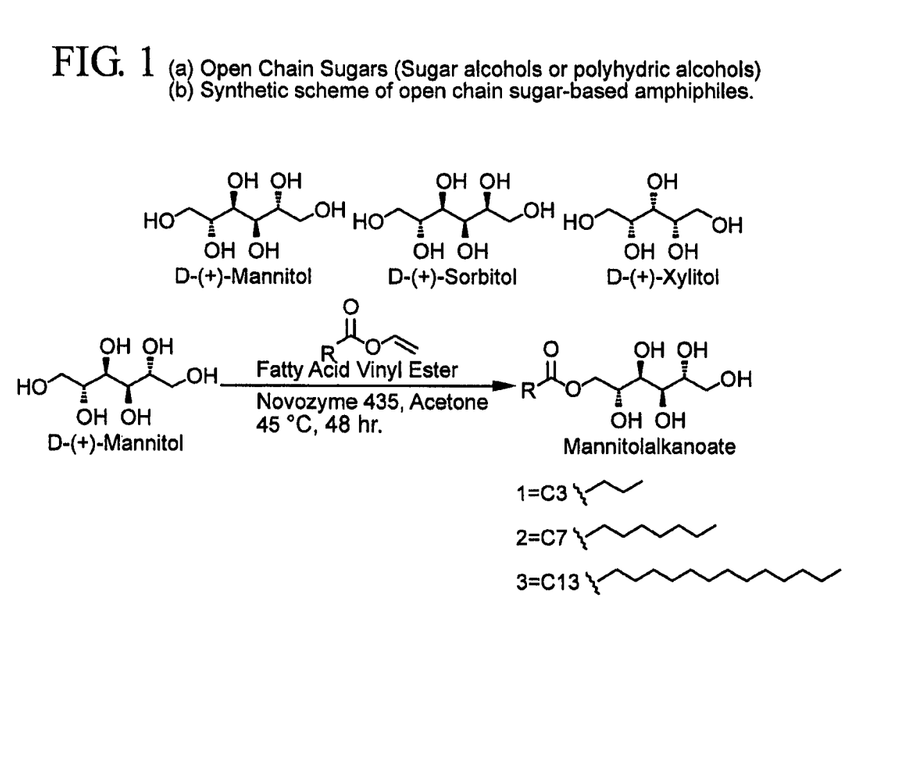
FIG. 1 Chemical structure of representative open chain sugars and synthesis scheme of sugar amphiphiles. a, Chemical structures of open chain sugars. b, General synthesis scheme for synthesis of open chain sugar amphiphiles.

The typical synthesis scheme for MGs is shown in FIG. 1b. Open-chain sugars, were regioselectively acylated at one or two of their primary hydroxyl groups. The process is a single-step enzyme mediated trans-esterification reaction of the sugar and a fatty acid donor using Novozyme 435. The overall yield is approximately 70% for all derivatives. Tuning of hydrophobicity is achieved by using fatty acids of different alkyl chain lengths; butyric acid ($C_4$), caprylic acid ($C_8$) and myristic acid ($C_{14}$) derivatives were synthesized for all the three sugars. The developed amphiphiles are typically denoted by a letter followed by a number, e.g., M8 is an amphiphile having a mannitol head and a $C_8$ tail.

Of the various sugar amphiphiles, the mannitol derivative M8 and the sorbitol derivative S8 were found to be organogelators, capable of gelling a wide range of organic liquids, including crude oil fractions and vegetable oils. The gelation capabilities of these amphiphiles are summarized in Table S1 (see Supplementary Information). Minimum gelation concentrations (MGC) for the gelators ranged from 1.5 to 5 wt % depending on the gelator and solvent. To characterize the thermal stability of the gels, gel-to-sol transition temperatures ($T_{gel}$) were determined and were in the range of 82-125° C. for 5 wt % M8 gels and 38-69° C. for 5 wt % S8 gels, depending on the solvent (see Supplementary Table S2). All the above gels were stable for months. The MGC and $T_{gel}$ values indicate that mannitol-based gelators are more efficient compared to those from its stereoisomer, sorbitol. Mannitol and sorbitol only differ in terms of the stereochemistry of the hydroxyl group at the $C_2$ position of sugar moiety (FIG. 1a). Thus, subtle changes in molecular chirality can greatly impact the gelation ability. Also, the MGC values are considerably lower for the 8 derivatives than the 4 derivatives. The gelling abilities of M8 and S8 were also investigated on crude oil fractions. As seen in Table S1, these gelators precipitated out from smaller chain hydrocarbons (hexane and heptane) but formed gels in longer chain hydrocarbons (mineral oil, silicone oil, and pump oil). The gelators were able to gel high boiling crude oil fractions (MGC~1 to 5% wt/v) more interestingly M8 could gel diesel at concentration as low as 2.5% wt/v indicating that it was able to immobilize diesel at-least 20 times of its weight.

In comparison to the mannitol and sorbitol derivatives, those of xylitol were ineffective at gelation under the given conditions. Among X4 and X8, only X8 was obtained as a solid powder. This powder could be dissolved in organic liquids at high temperatures, but it precipitated out from the liquids when cooled to room temperature. Structurally, xylitol has one less hydroxyl group compared to mannitol and sorbitol (FIG. 1a), which evidently affects the self-assembly of its derivatives in organic solvents. Moreover, 14 derivatives of all the three sugars (i.e., M14, S14 and X14) were also ineffective at gelation under the given conditions. These materials could be homogeneously solubilized in organic liquids, both at high and low temperatures, but the liquids were not gelled. Thus, our studies show that a moderate chain length (~8) is optimal for gelation. The efficient M8 and S8 amphiphiles were chosen for further studies.

Figure 2A:
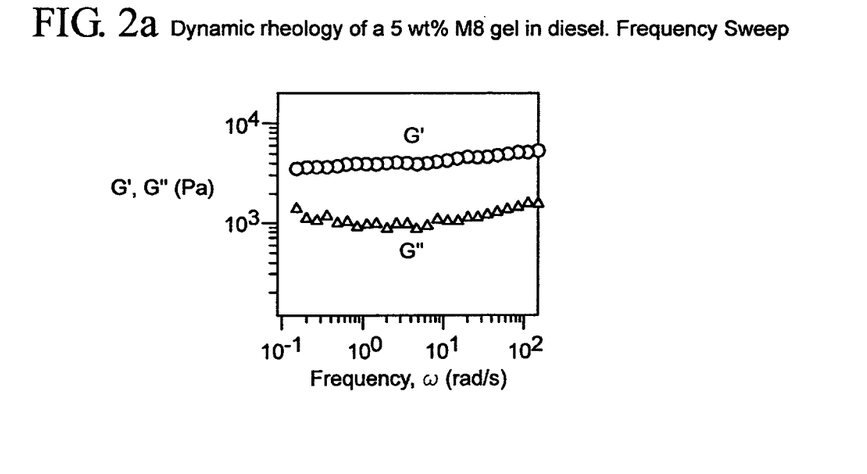
FIG. 2 Optical Microscopic pictures of self-assembled aggregates open chain sugar amphiphiles in canola oil matrix. a, Normal cooling and b, Slow cooling of an M8-canola oil isotropic solution. c, Normal cooling and d, Slow cooling of an S8-canola oil isotropic solution. e, Normal cooling and f, Slow cooling of an X8-canola oil isotropic solution.
Figure 2B:
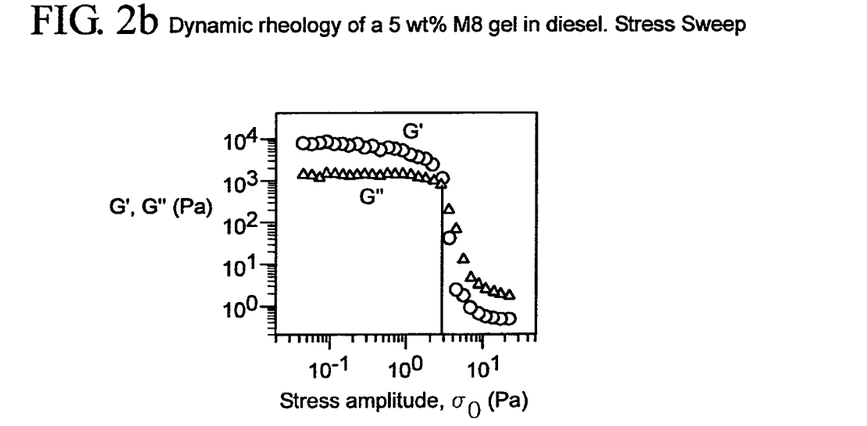

Rheological studies on M8 and S8 gels revealed the typical response expected of organogels. FIG. 2 shows dynamic rheological data for a gel of 5 wt % M8 in diesel. FIG. 2a is the frequency spectrum, where the elastic modulus G' and the viscous modulus G" are plotted as functions of the angular frequency ω. Note that G' is independent of frequency and considerably higher than G" over the entire range of frequencies. Such a response is characteristic of a gel because it shows that the sample does not relax over very long time scales. The gel modulus (value of G') is a measure of the gel stiffness. For the 5% M8 gel, the gel modulus is ~4000 Pa, which and shows that the gel is quite stiff. FIG. 2b is a plot of the moduli G' and G" as functions of the stress amplitude $\sigma_0$. Both moduli are independent of stress at low $\sigma_0$ (this regime is the linear viscoelastic regime) but decrease at higher $\sigma_0$. The critical value of $\sigma_0$ at which a sharp decrease in moduli occurs is the yield stress of the gel and its value in the present case is ~30 Pa. This value is sufficiently high to support the weight of the gel in an inverted vial. Similar results were observed with a 5% gel of S8 in diesel and in this case, the gel modulus was 2000 Pa and the yield stress was again close to 30 Pa.

Figure 3A:
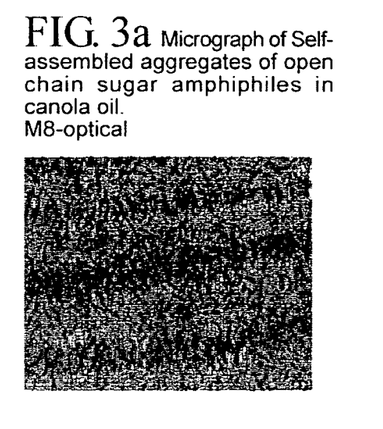
FIG. 3 SEM images Open chain sugar gels. a, M8-toluene gel at 2.5% wt/v concentration. b, Phase selective M8-toluene gel at 2.5% wt/v developed from toluene-water mixture by conventional heating method. c, Phase selective M8-toluene gel 2.5% wt/v developed from toluene-water mixture by new method d, S8 toluene gel at 3.5% wt/v concentration and e, Crystalline precipitate of X8 from cyclohexane.
Figure 3B:
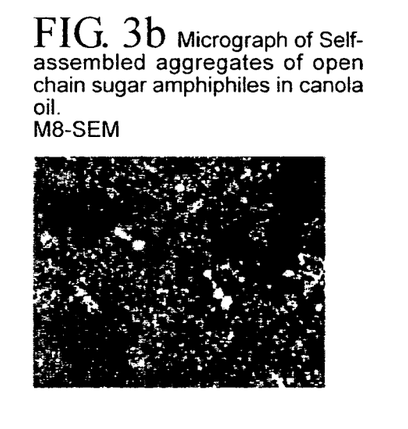
Figure 3C:
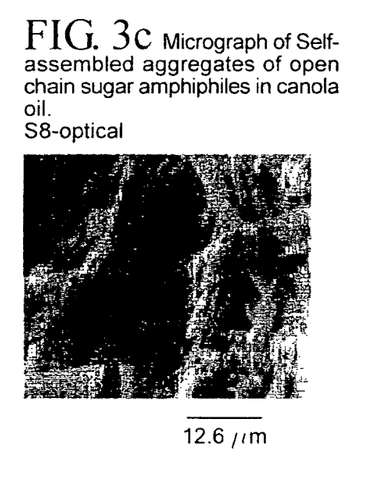
Figure 3D:
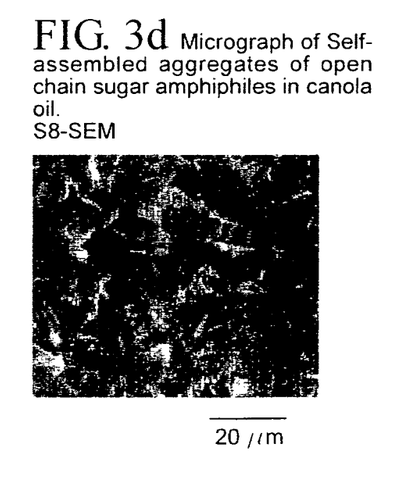

The morphologies of M8 and S8 gels were characterized using optical and electron microscopy. Results are provided in FIG. 3 for gels of the above gelators in a vegetable (canola) oil matrix. Gels of the mannitol derivative M8 show highly branched fibers (FIG. 3a), whereas gels of the sorbitol derivative S8 reveal mostly platelet structures along with spherulitic clusters (FIG. 3b). Similar results were observed in all organic solvents (see Supplementary FIG. S3). SEM images of M8 and S8 gels in toluene are consistent with the optical microscopy results. The SEM image of the M8 gel (FIG. 3c) shows that the fibers are actually flat ribbons having a width ~100 nm and the gel is presumably an entangled mesh of these ribbons. In contrast, the S8 gel consists of clustered crystalline platelets (FIG. 3d). Note that the ribbon morphology of M8 is much more conducive to gelation (entrapment of solvent) than the spherulitic morphology of S8 and this explains the lower MGC and higher $T_{gel}$ for the former.

Figure 4:
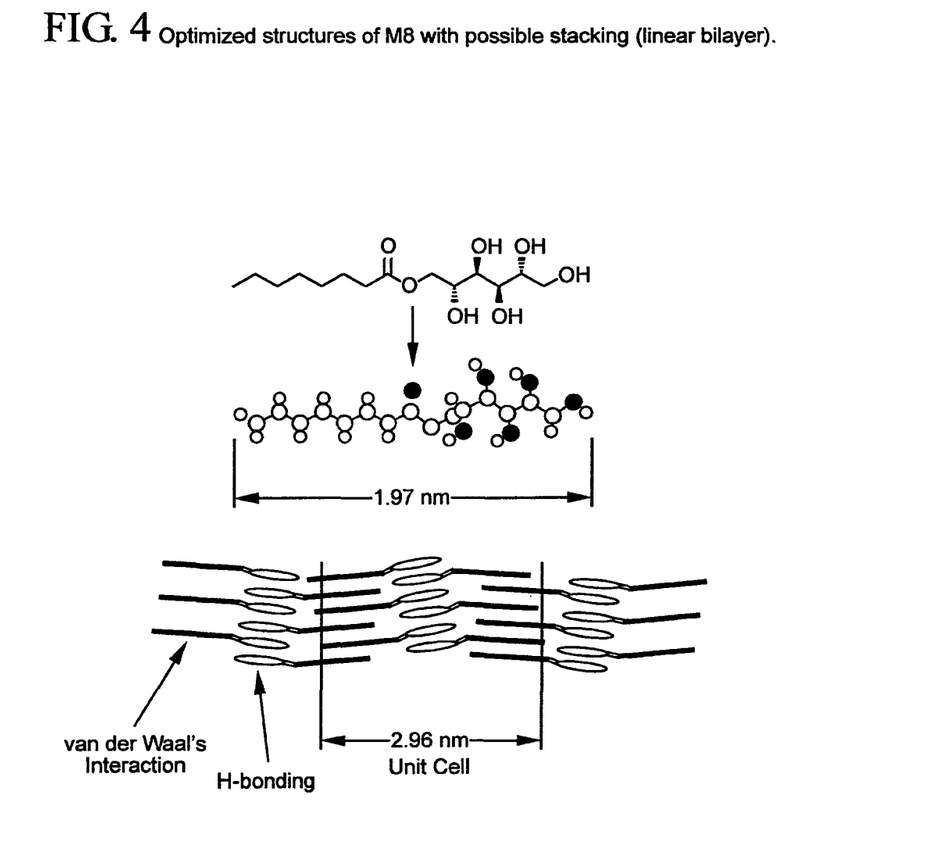
FIG. 4 Possible Bialyers conformation of open chain sugar. a, Optimized structures of M8 with possible stacking (linear bilayer). b, Optimized structures of S8 with possible stacking (curved bilayer)

To elucidate the gel structure in detail, X-ray diffraction (XRD) experiments were conducted on both the gelator powders as well as the corresponding gels. Powder form of M8 and S8 exhibit lamellar stacking pattern, i.e., with Bragg spacing between subsequent peaks in the ratio of 1:2:3 etc. (see Supplementary FIG. S6). The periodicity, long d-spacing, of lamellar structure was found to be 2.96 and 2.38 nm for M8 and S8 respectively. XRD spectra on gels of M8 and S8 also show primary peaks close to the above d-spacing; for M8-gels it was ~2.98 nm and S8 gels it was ~2.46 nm (independent of the nature of the organic liquid). The similarity in the XRD data for the gels and the solid gelator indicate that the molecules are packed in a similar way in both states. In agreement with previous studies, the above d-spacings in the gels are correlated to the sizes of the respective bilayers (FIG. 4). For example, the length of a single M8 molecule, deduced from optimized geometry calculations, is 1.97 nm, assuming the alkyl tail is fully extended. A bilayer of such molecules, arranged in tail-head-head-tail fashion, will have a thickness less than twice this length if the tails are flexible. This result is consistent with the observed d-spacing of 2.98 nm.

The arrangement of the amphiphilic M8 molecules within a bilayer is shown in FIG. 4. The alkyl tails from individual molecules are on the outside, i.e., in contact with the non-polar solvent, while the hydrophilic sugar heads form the interior of the bilayer. In other words, the bilayer structure is reversed compared to that in water. The weak non-covalent interactions responsible for bilayer formation include van der Waals interactions between the alkyl tails as well as hydrogen bonding between the sugar headgroups. Hydrogen bonding, and hence hydroxyl group, is believed to play a constructive role in the formation of a network capable of entrapping solvents. IR spectra were obtained on the sols of M8 and S8 as well as on the same samples after they had gelled upon cooling. A distinct shift observed in the wave numbers corresponding to hydroxyl groups between the sol and gel states indicates the participation of these groups in hydrogen bonding (FIG. S5, Supplementary Information). This supposition was also confirmed by blocking the hydroxyl groups through benzylidene complex formation. The benzylidene complex of M8 was not able to gel organic liquids—rather it was easily soluble in the organic liquids. Again, this shows the crucial importance of hydrogen bonding in gel formation.

The ability of M8 and S8 gelators for phase selective gelation (PSG), specifically, their ability to gel the oil phase from an immiscible mixture of oil and water was studied. In initial experiments, a given gelator powder was added to an immiscible mixture of water and mixture (equal amounts on a volume basis) and the mixture was heated to dissolve the gelator. The mixture was then vortexed at 1000 rpm for around 10 min and allowed to settle down. Initially after vortexing, the sample had a milky white appearance, indicative of a fine dispersion of oil in water. Eventually, the sample separated into two layers, the top layer being gelled oil and the bottom layer being liquid (ungelled) water. Similar results showing PSG were obtained regardless of the oil:water ratio. A variety of solvents could be gelled in a phase-selective manner, including crude oil fractions (alkanes with carbon atoms n≥7, diesel, pump oil) and edible oils.

Figure 5:
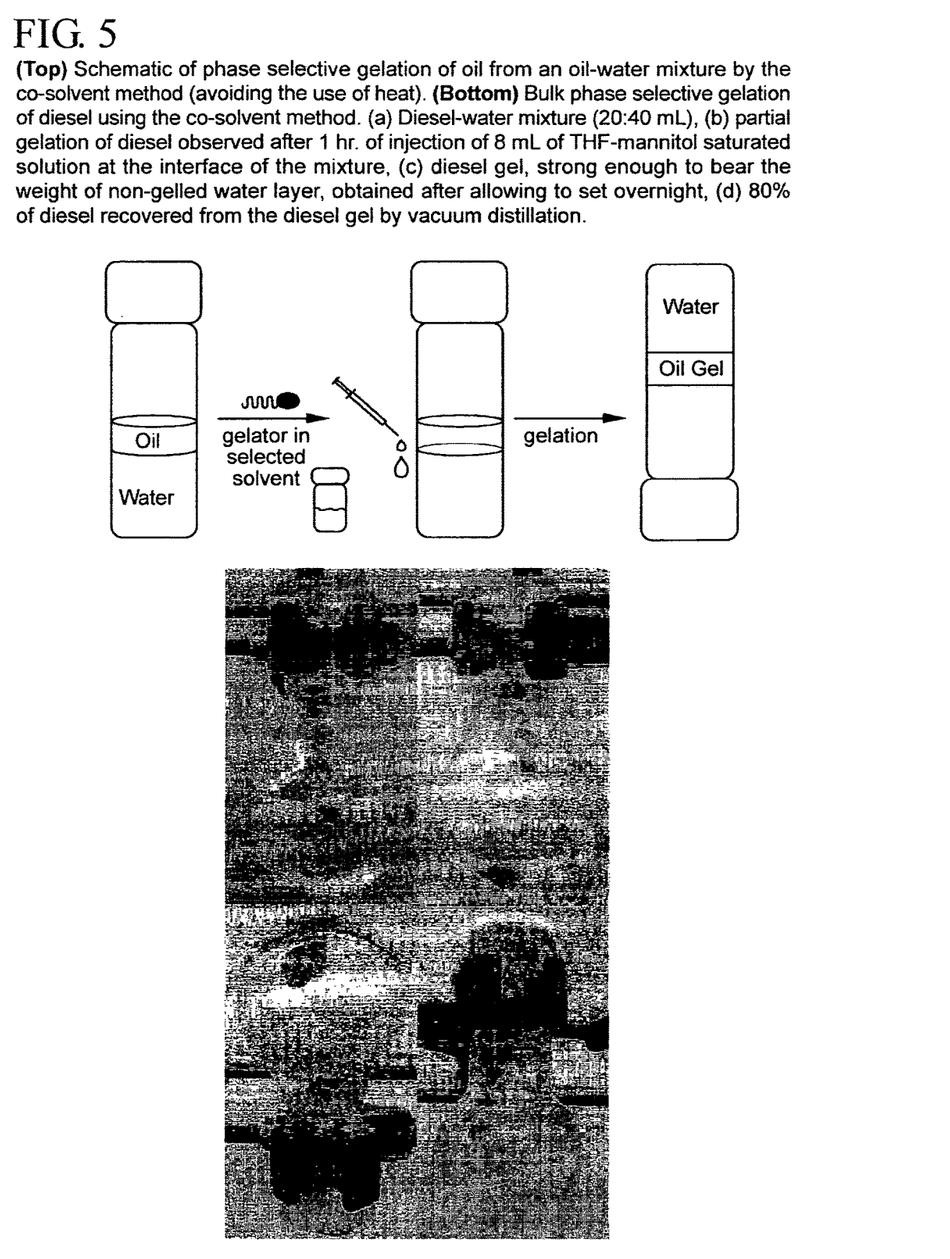
FIG. 5 Schematic representation of phase selective gelation of organic liquid from organic liquid-water mixture by conventional heating method and by new method.

Various methods that did not involve heat were tested. The gelator was first dissolved in a solvent that is miscible with water. The gelator-solvent solution was then injected or sprayed onto the oil/water mixture at room temperature. The solvent should have high solvating power for the gelator while being miscible in water. Numerous solvents were tested and several of them were found to work, including alcohols (methanol, ethanol, iso-propanol, tert-butanol), dioxanes and THF. Ethanol or THF was chosen for further studies. A schematic of PSG using the solvent method is depicted in FIG. 5. Both M8 and S8 could form phase selective gels by this method, but the gels with M8 were stronger under the given conditions. That is, in the case of M8, the MGCs required for bulk gelation as well as PSG of given oils were identical. In contrast, the MGC of S8 to form a phase-selective gel was much higher than that required to form a bulk gel in the same solvent.

Phase selective gelation using M8 and the solvent method with THF was demonstrated with a variety of organic solvents such as toluene, diesel, cooked oil and mineral oil. Gel formation in the oil phase was not affected by the nature of the aqueous environment: e.g., whether the water was acidic or basic, saturated with NaCl or $CaCl_2$, or if the water contained small quantities of soaps or detergents. Depending on the concentration of M8 delivered through the solvent method, gels with varying strengths were obtained. For a concentration equal to 5 wt % M8 in diesel, the gelled oil had a sufficient yield stress to bear not only its own weight but the weight of the water layer as well upon inversion of the container or vial. Rheological studies on the gelled oil layer (data not shown) gave similar data as for the bulk gel at the same concentration (FIG. 2) with similar values of gel modulus G' and yield stress. The method of phase selective gelation under ambient conditions works very well for a variety of organic liquids and at different environments.

An additional consideration is the ability to recover the oil from the gelled material and also the ability to recover and reuse the gelator itself. Experiments were carried out involving PSG of diesel using M8 as shown in FIG. 5. A diesel-water mixture (20:40 mL, FIG. 6a) was prepare to which an 8 mL aliquot of the M8-THF solution was added (thereby delivering 1 g of M8, which is 5 wt % based on the diesel volume). The diesel layer solidified appreciably within 2 h (FIG. 6b). After 24 h, the gel was strong enough to bear the weight of the 40 mL of water as well upon inversion of the container (FIG. 6c). Next, the bottom water layer was injected out from the container and the gel was gradually heated to 125° C. under vacuum. The gel slowly transformed into a sol and the diesel was then distilled off. Approximately 80% of the diesel (FIG. 6d) could be recovered by this process. The residue in the container was characterized by thin layer chromatography (TLC) and was found to be mostly the M8 gelator with a small amount of diesel and degraded product. This residue was able to selectively gel 10 mL of diesel again, which indicates the reusability of the gelator.

An alternative to vacuum distillation for diesel recovery is enzyme-mediated gel degradation. A hydrolase enzyme (Lipolase 100 L, Type EX, lipase units 100 KLU/g) was used to cleave the ester linkages between the fatty acid moiety and the mannitol unit in M8. As a result, the non-covalent bonds between gelator molecules are broken and the gel is liquefied back to diesel. While the gelator is not available for further use, one advantage of enzyme-mediated degradation is that it can be accomplished at room temperature.

In conclusion, short chain, amphiphilic open chain sugar organogelators were successfully synthesized using regioselective enzymatic trans-esterification method. The organogels produced using the sugar gelators were characterized and gelators were hypothesized to self-assemble in lamellar form in the gels. Moreover, the organogelators exhibited efficient PSG of wide array of organic liquids including crude oil fractions. Further, to induce gelation at room temperature a new method was formulated. The application of a new method and phase selective gelation of open chain sugar gelators was demonstrated in recovering oil spills and hence for environmental clean-up. Selective gelation of diesel from diesel-water mixture using M8 derivative and recovery of diesel from the gel was demonstrated by either vacuum distillation or enzyme-mediated gel degradation process. The recycling ability of the gelators in recovering oil spills was also demonstrated.

The following article is incorporate by reference in its entiretly: Jadhav, Swapnil, et al. "Sugar-Derived Phase-Selective Molecular Gelators as Model Solidifiers for Oil Spills" Angewandte Chemie International Edition, 2010, available online at http://dx.doi.org/10.1002/anie.201002095

EXAMPLES

Example 1

Enzyme Catalytic Method for Regioselective Esterification of Open Chain Sugars.

To a mixture of mannitol (0.546 g, 3 mmol), vinyl esters (9 mmol; vinyl butyrate, vinyl caprylate and vinyl myristate) and activated molecular sieves (10 g) in dry acetone (40 mL) was added Novozyme 435 (0.35 g). The reaction mixtures were shook at 200 rpm in incubator shaker at 45° C. for 48 hr. The reaction mixtures were analyzed by TLC for completion of the reaction, later filtered and concentrated. The obtained crude products were purified by silica gel flash chromatography using chloroform:methanol (9:1) as an eluent, afforded pure products as white solid. The yields were above 70% for all the reaction. Similar results are obtained when the open chain sugar is sorbitol.

Example 2

Gelation Method for MGs.

Typically, gelator (5 mg) was added to a 2 mL scintillation vial containing 100 μL of the required organic liquid. The vial was heated and agitated until the solid was completely dissolved. The resulting homogenous solution was allowed to cool down to room temperature undisturbed. The gel state was said to be achieved if there was no gravitational flow observed on inverting the scintillation vial. To determine the maximum amount of organic liquid the gelator can gel, amount of organic liquid was increased in the increments of 50 μL until gravitational flow was observed. The ratio of gelator to organic liquid concentration is stated in % weight to volume format and is stated as minimum gelation concentration (MGC) of the gelators for that particular organic liquid.

Example 3

Gel Melting Temperature ($T_{GEL}$).

Gel melting temperature was determined by typical 'inversion tube method'. In a 2 mL scintillation vial gel was prepared by dissolving 0.5 wt % gelator in a required organic liquid and closed with tight screw cap. The vial was immersed in the oil-bath 'upside down' and slowly heated. The temperature at which the viscous gel melted down was recorded as Tgel.

Example 4

Optical Microscopy Studies.

A standard glass slide containing a small portion of gel was mounted on Leica DM LB2 microscope stage and the phase changes were observed with C-Span 10×PH1 phase contrast objective.

Example 5

Morphological Studies of the Gel Structure (SEM).

Scanning Electron Microscopic (SEM) images were recorded on Zeiss DSM 940 thermionic electron microscope at different magnifications. The morphology of the gels were studied from the samples prepared by drying under ambient conditions. Gold was coated on the gel samples prior to SEM analysis using a sputter coater.

Example 6

Infra-Red (IR) Spectroscopy.

IR spectroscopic analysis of the gel was performed using Nicolet 380 FT-IR spectrophotometer in ATR mode, while the liquid samples were sandwiched between NaCl plates.

Example 7

X-Ray Diffraction Studies.

A small portion of a gel sample was transferred in a sample holder and immediately the reflectance was measured. The XRD measurement was performed on PANalytical X'Pert PRO with MPD PW 3040/60 generator S/N DY 2974 and monochromatic Cu—Co radiation (45 kV, 40 A).

Example 8

Phase Selective Gelation (PSG) through Conventional Method.

Generally required organic liquids (300-700 μl) were taken in a 4 ml scintillation vial to that water (700-300 μl) was added. To the biphasic mixture gelator (1-1.5×MGC) was added. The entire mixture was heated (to dissolve gelator in organic liquid) and vortexed (to disperse the two phases uniformly). The vial was later allowed to set and cool to room temperature. The gel state of the organic liquid was confirmed when no gravitational flow was observed on inversion of vial.

Example 9

Phase Selective Gelation (PSG) through Aliquot Method.

Typically, an aliquot of gelator was prepared in a suitable solvent (THF was used for this application). In a scintillation vial biphasic mixture of required organic liquid (300-700 μL) and water (700-300 μL) was taken. The prepared aliquot, capable of delivering 1-1.5×MGC concentration, was injected at the interface and allowed to set. Again the gel state was confirmed when no gravitational flow was observed on inversion of the vial.

Example 10

Encapsulation of a Hydrophilic, Pharmaceutically Active Ingredient.

10 mg caffeine is mixed with 1 g canola oil and 0.015 g mannitoloctanoate at 90° C. Upon cooling, the solution thickens or gels, so the canola oil encapsulates the caffeine. Similar results are obtained when the amphiphilic ester is sorbitoloctanoate.

Example 11

Encapsulation of a Lipophilic, Pharmaceutically Active Ingredient.

2 g curcumin is mixed with 20 g triglyceride and 0.5 g mannitoloctanoate at 75° C. Upon cooling, the solution thickens or gels, so the triglyceride encapsulates the curcumin. Similar results are obtained when the amphiphilic ester is sorbitoloctanoate.

Example 12

Gelling Crude Oil to Facilitate Transportation.

1 kg of crude oil is mixed with 0.03 kg mannitoloctanoate at ambient temperature. The liquid crude oil forms a gel with the addition of the mannitoloctanoate. The gelled crude oil is transported by truck. Spills are prevented by gelling the crude oil. Similar results are obtained when the open chain sugar is sorbitol.

Example 13

Formation of a Microemulsion.

10 mg of mannitoloctanoate is mixed with a mixture of 1 mL of canola oil and 3 mL of water (pH=7-8). The mixture of is sonicated and vortexed for adequate time to yield a translucent microemulsion. Similar results are obtained when the open chain sugar is sorbitol.

The invention claimed is:

1. A method for phase selective gelling a hydrophobic liquid comprising:
   contacting a liquid mixture having a hydrophobic liquid phase and an aqueous phase with an amphiphilic ester having the formula $RO[C(O)R^1]_m$, wherein:
   RO— represents a moiety of a sugar alcohol a monosaccharide or a disaccharide;
   $R^1$ independently represents a branched or unbranched, saturated or unsaturated alkyl group having a minimum of 2 and a maximum of 20 carbon atoms;
   m is 1 or 2; and
   the amphiphilic ester comprises at least 1.5%-10% of the liquid mixture;
   to provide a gel; and
   wherein contacting and gel formation occur at ambient temperature.

2. A method according to claim 1, wherein RO represents a moiety of a sugar alcohol of a monosaccharide.

3. A method according to claim 2, wherein RO represents a moiety of a 6-carbon sugar alcohol.

4. A method according to claim 3, wherein the sugar alcohol is mannitol or sorbitol.

5. A method according to claim 4, wherein $R^1$ has seven carbon atoms.

6. A method according to claim 1, wherein RO represents a moiety of a disaccharide.

7. A method according to claim 1, wherein the alkyl group is saturated and unbranched.

8. A method according to claim 1, wherein m is 2.

9. A method according to claim 1, wherein $R^1$ has seven carbon atoms.

10. A method according to claim 1, wherein the hydrophobic liquid is a fatty acid or a glyceride.

11. A method according to claim 1, wherein the hydrophobic liquid is selected from the group consisting of a vegetable oil, a fish oil, an insect pheromone, or an essential oil.

12. A method according to claim 11, wherein the hydrophobic liquid is a vegetable oil.

13. A method according to claim 1, wherein the hydrophobic liquid is crude oil.

14. A method according to claim 13, wherein the method occurs at ambient temperature.

15. The method according to claim 4, wherein R1 has eight carbon atoms.

16. The method according to claim 1, wherein the amphiphilic ester comprises 1.5-5% of the liquid mixture.

17. A method for phase selective gelling liquid petroleum comprising:
   contacting a liquid mixture having a liquid petroleum phase and an aqueous phase with an effective amount of an amphiphilic ester having the formula RO[C(O)R1]m, wherein:
   RO— represents a moiety of a sugar alcohol, a monosaccharide or a disaccharide;
   R1 independently represents a branched or unbranched, saturated or unsaturated alkyl group having a minimum of 2 and a maximum of 20 carbon atoms; and
   m is 1 or 2;
   to provide a gelled liquid petroleum; and
   wherein contacting and gel formation occur at ambient temperature.

18. The method according to claim 17, wherein liquid petroleum is selected from the group consisting of crude oil, gasoline, kerosene, diesel fuel, heavy gas oil, and lubricating oil.

19. A method according to claim 17, wherein the sugar alcohol is mannitol or sorbitol.

* * * * *